(12) United States Patent
Kanebako et al.

(10) Patent No.: US 8,097,275 B2
(45) Date of Patent: Jan. 17, 2012

(54) EXTERNAL SKIN PATCH

(75) Inventors: Makoto Kanebako, Fuji (JP); Gou Yanagimoto, Fuji (JP); Toru Watanabe, Toyama (JP); Shouichi Hasegawa, Toyama (JP)

(73) Assignees: Kowa Company, Ltd., Nagoya-shi, Aichi (JP); Maeda Pharmaceutical Co., Ltd., Toyama-shi, Toyama (JP)

( * ) Notice: Subject to any disclaimer, the term of this patent is extended or adjusted under 35 U.S.C. 154(b) by 349 days.

(21) Appl. No.: 12/428,663

(22) Filed: Apr. 23, 2009

(65) Prior Publication Data
US 2010/0003312 A1 Jan. 7, 2010

(30) Foreign Application Priority Data

Apr. 23, 2008 (JP) ................................. 2008-112727
Jan. 27, 2009 (JP) ................................. 2009-015638

(51) Int. Cl.
*A61K 9/70* (2006.01)
*A61K 47/30* (2006.01)

(52) U.S. Cl. ..................................... 424/447; 514/772.3

(58) Field of Classification Search ........................ None
See application file for complete search history.

(56) References Cited

U.S. PATENT DOCUMENTS 5,106,625 A * 4/1992 Yamamoto et al. ........... 424/401

FOREIGN PATENT DOCUMENTS

| JP | 05-139961 | 6/1993 |
|---|---|---|
| JP | 06-145047 | 5/1994 |
| JP | 06-145053 | 5/1994 |
| JP | 06-219941 | 8/1994 |
| JP | 08-175979 | 7/1996 |
| JP | 08-295624 | 11/1996 |
| JP | 11-302160 | 11/1999 |
| JP | 2000-128780 | 5/2000 |

OTHER PUBLICATIONS

JP06-145053 (1994), Machine Translation, retrieved on Jan. 4, 2011 from JPO.*

* cited by examiner

*Primary Examiner* — Tracy Vivlemore
*Assistant Examiner* — Jennifer Berrios
(74) *Attorney, Agent, or Firm* — Knobbe, Martens, Olson & Bear, LLP

(57) ABSTRACT

An object of the invention is to provide a hydrous external skin patch, which has adherence sufficient for adhering to an affected area for several times without using an auxiliary tape or the like and is excellent in utility so that the patch can be easily peeled off even if the paste adheres to itself before application to the affected area.

The hydrous external skin patch is characterized in that a paste of the patch comprises 0.1 to 10 wt % of a drug, 0.1 to 20 wt % of an adhesive base, 0.001 to 3.0 wt % of a crosslinker, 15 to 60 wt % of water, 2 to 20 wt % of a tackifier resin, 0.4 to 10 wt % of a dissolving agent for the tackifier resin, 0.1 to 30 wt % of an oil absorbing inorganic powder, and 0.1 to 20 wt % of a dextrin fatty acid ester and has a thickness of 100 to 1,000 μm.

7 Claims, 2 Drawing Sheets

EXTERNAL SKIN PATCH

BACKGROUND OF THE INVENTION

1. Field of the Invention

The present invention relates to an external skin patch, particularly to a hydrous external skin patch excellent in adherence and utility.

2. Description of the Related Art

In general, gel-like ointments, creams, liquids, patches, and the like are practically used as external skin preparations. Of those, the patches are effective preparations for treatment of affected areas which are usually covered with clothes (such as shoulder and back) because the patches can retain the effects of drugs for several hours per one-time use.

The patches may be broadly divided into non-aqueous adhesives and aqueous adhesives. Non-aqueous adhesives are plasters, plaster agents, and tapes which include a rubber adhesive, an acrylic (emulsion) adhesive, a silicon adhesive, or the like and do not substantially contain water. Aqueous adhesives are cataplasms which include a water-soluble acrylic adhesive and contain water at a relatively high level.

The non-aqueous adhesive has an advantage of high adherence, and high flexibility because of its small thickness of the paste (the total thickness of the support and the adhesive layer is 1 mm or less), for example. However, the non-aqueous adhesive has disadvantages of irritation to skin due to high occlusion degree of the preparation and peeling from skin particularly during sweating because the preparation includes a hydrophobic adhesive.

On the other hand, the aqueous adhesive has an advantage of low irritation to skin because the adhesive contains water at a high level. However, the aqueous adhesive has disadvantages of relatively low adherence, significantly lowered adherence due to evaporation of water, low flexibility because of the large thickness of the paste (the total thickness of the support and the adhesive layer is 1.5 mm or more), and dropping due to the weight of the preparation when the preparation absorbs an excessive amount of sweat, for example.

Moreover, there are also known novel hydrous patches containing both a non-aqueous adhesive and an aqueous adhesive (Patent Documents JP 06-145047 A and JP 06-145053 A). However, such novel hydrous patches also have insufficient adherence and contain a paste having low water absorbing ability, and hence tend to be easily peeled off particularly during sweating. In addition, the patches have a disadvantage that adhesion of the paste to itself before application to an affected area may make the patches unusable.

Although various studies have been made on enhancement of the adherence of patches (Patent Documents JP 05-139961 A, JP 06-219941 A, JP 08-295624 A, JP 11-302160 A, JP 08-175979 A and JP 2000-128780 A), all the methods are unsatisfactory because of insufficient adherence and complex production methods.

SUMMARY OF THE INVENTION

Therefore, an object of the present invention is to provide a hydrous external skin patch, which has adherence sufficient for adhering to an affected area for several times without using an auxiliary tape or the like and is excellent in utility so that the patch can be easily peeled off even if the paste adheres to itself before application to the affected area.

Accordingly, the inventors of the present invention have made extensive studies to overcome failings of a conventional hydrous external skin patch, which includes, as essential components, a drug, an adhesive base, a crosslinker, water, a tackifier resin and a dissolving agent for the tackifier resin, and an oil absorbing inorganic powder, and as a result, the inventors have found out that, if a dextrin fatty acid ester is blended in the paste of the patch, it is possible to provide a hydrous external skin patch which has improved adherence and can be easily peeled off even if the paste adheres to itself before application to the affected area, thus completing the present invention.

That is, the present invention provides a hydrous external skin patch, characterized in that a paste of the patch comprises 0.1 to 10 wt % of a drug, 0.1 to 20 wt % of an adhesive base, 0.001 to 3.0 wt % of a crosslinker, 15 to 60 wt % of water, 2 to 20 wt % of a tackifier resin, 0.4 to 10 wt % of a dissolving agent for a tackifier resin, 0.1 to 30 wt % of an oil absorbing inorganic powder, and 0.1 to 20 wt % of a dextrin fatty acid ester and has a thickness of 100 to 1,000 μm.

The hydrous external skin patch of the present invention has improved adherence to skin, and hence failings of a conventional hydrous external skin patch, such as riding up and dropping, have been overcome. Even if the paste of the patch adheres to itself before application to an affected area, the patch can be easily peeled off and used again and hence is economically useful. Moreover, even if the patch is used in summer or outdoor activities where excessive sweating occurs, the patch maintains sufficient adherence and hence is not required to be fixed with an auxiliary tape or the like.

DESCRIPTION OF THE EMBODIMENT

Figure 1:
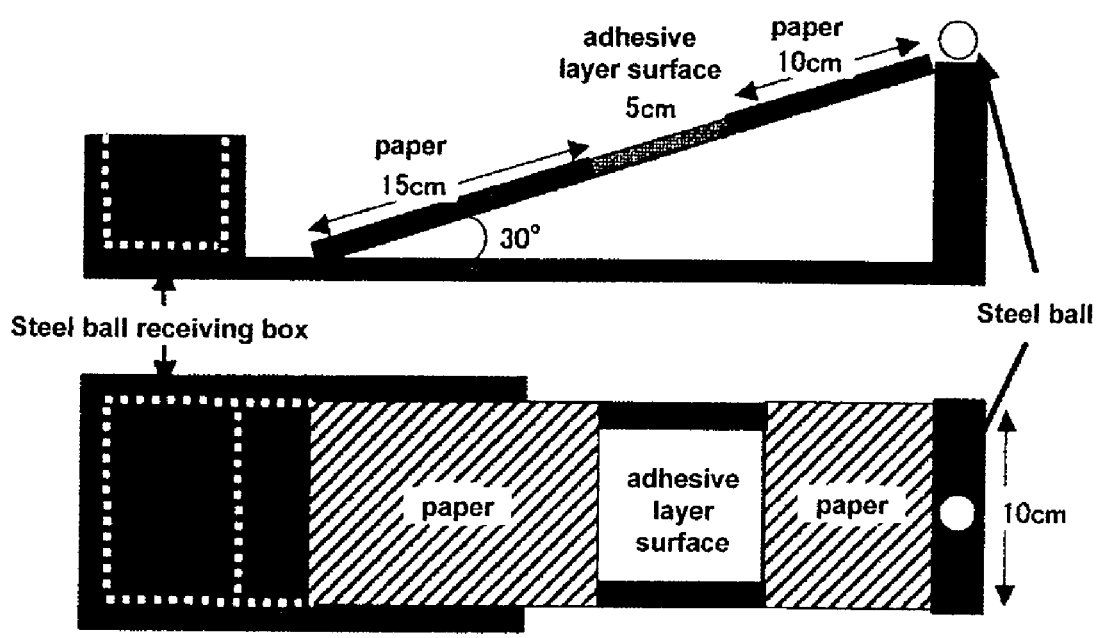
FIG. 1 is a schematic view illustrating a device used in an adhesion test (i)

The dextrin fatty acid ester used in the present invention is an ester compound synthesized from dextrin and fatty acid. The dextrin part is a collective term of intermediate products of decomposition of starch into maltose or dextrose, and examples thereof include amylodextrin (iodine reaction: indigo blue, specific optical rotation: +190 to +195°, molecular weight: >10,000), erythrodextrin (iodine reaction: red to brown, specific optical rotation: +194 to +196°, molecular weight: 6,200 to 7,000), achrodextrin (iodine reaction: pale brown, specific optical rotation: +192°, molecular weight: 3,700), and maltodextrin (iodine reaction: colorless, specific optical rotation: +181 to +183°) (Guide Book of Japanese Pharmacopoeia Fifteenth Edition). Of those, a compound which turns purple to red-brown in an aqueous solution of a dextrin fatty acid ester in accordance with the "dextrin palmitate" identification test 2 of Japanese Pharmaceutical Excipients (hereinafter, also referred to as "JPE") is preferable. Meanwhile, the fatty acid part of the dextrin fatty acid ester is preferably a fatty acid having 12 to 22 carbon atoms and more preferably a saturated fatty acid thereof. Further, the acid value of the dextrin fatty acid ester is preferably 38 or less (mgKOH/g) when the dextrin fatty acid ester is dissolved in a 95% ethanol/xylene mixture (1:1) in accordance with the acid value test method of JPE.

Examples of the dextrin fatty acid ester include dextrin palmitate, dextrin stearate, dextrin behenate, dextrin myristate, dextrin coconut oil fatty acid, and dextrin laurate. Of those, dextrin palmitate and dextrin myristate are preferred and dextrin palmitate is particularly preferred. The dextrin palmitate is available as a commercial product such as Rheopearl KL2, Rheopearl KS2, and Rheopearl TL2 (manufactured by Chiba Flour Milling Co., Ltd.), and dextrin palmitate (manufactured by Nikko Chemicals, co., Ltd.). The dextrin myristate is available as a commercial product such as Rheopearl MKL2 (manufactured by Chiba Flour Milling Co., Ltd.). Those dextrin fatty acid esters may be used singly or in an appropriate combination of two or more kinds of them.

To give an adhesion enough to adhere to an affected area for a long period of time and an adhesion appropriate for easy peeling of a paste which adheres to itself, the dextrin fatty acid ester content is preferably 0.1 to 20 wt %, more preferably 0.5 to 10 wt %, particularly preferably 0.5 to 7.0 wt %, and most preferably 0.5 to 5.0 wt % with respect to the weight of the paste.

Examples of the drug that can be used in the present invention include: local stimulating agents such as methyl salicylate, glycol salicylate, camphor, menthol, chili pepper extract, and vanillylamide nonylate; peripheral blood flow-improving agents such as tocopherol acetate and tocopherol nicotinate; antihistamines such as diphenhydramine, chlorpheniramine maleate, and isothipendyl hydrochloride; extract or powder of antiphlogistic herbal medicines such as Angelica root, Phellodendron bark, *Gardeniae fructus, Arnica montana*, and *Aesculus hippocastanum* seed; nonsteroidal antiinflammatory agents such as glycyrrhetinic acid, indomethacin, piroxicam, ketoprofen, flurbiprofen, felbinac, loxoprofen, and diclofenac; external steroids such as prednisolone, hydrocortisone, dexamethasone, and fluocinolone acetonide; antipruritic agents such as crotamiton; topical anesthetics such as lidocaine and dibucaine; and disinfectants such as chlorhexidine gluconate, cetylpyridinium chloride and benzalkonium chloride. Of those, nonsteroidal antiinflammatory agents are preferred and indomethacin is particularly preferred. The content of the drug may be in such a range that pharmacologic effects can be generally exhibited in patches and preferably 0.1 to 10 wt % and particularly preferably 0.5 to 5 wt % with respect to the weight of the paste.

The adhesive base used in the present invention is a base having adherence property in moisture state, and examples thereof include a substance obtained by polymerizing acrylic acid (polyacrylic acid), a substance obtained by partially neutralizing and polymerizing acrylic acid (partially neutralized polyacrylic acid), and a substance obtained by completely neutralizing and polymerizing acrylic acid (completely neutralized polyacrylic acid). The base is contained to enhance the adherence property of the paste. In particular, the substance obtained by partially neutralizing and polymerizing acrylic acid has a neutralization degree of preferably 70 mol % or less, more preferably 60 mol % or less, and particularly preferably 50 mol % or less. Further, from a productivity standpoint, the neutralization degree is preferably 10 mol % or more. Examples of commercial products of the polyacrylic acid include Julimer AC-10L (manufactured by Nihonjunyaku Co., Ltd.) and AQUALIC HL (manufactured by Nippon Shokubai Co., Ltd.). Examples of commercial products of the partially neutralized polyacrylic acid include Viscomate NP-600, Viscomate NP-700, and Viscomate NP-800 (manufactured by Showa Denko K. K.), Aronbis 105X and Aronbis 106X (manufactured by Nihonjunyaku Co., Ltd.). Examples of commercial products of the completely neutralized polyacrylic acid (sodium polyacrylate) include Aronbis S (manufactured by Nihonjunyaku Co., Ltd.), Polystar A-1060 (manufactured by NOF Corporation), Viscomate F-480SS (manufactured by Showa Denko K. K.), and AQUALIC FH (manufactured by Nippon Shokubai Co., Ltd.). The polyacrylic acid, partially neutralized polyacrylic acid, and completely neutralized polyacrylic acid may be used singly or in combination of two or more.

The adhesive base content may be in a range generally sufficient for imparting an adhesion required for the patch and is preferably 0.1 to 20 wt % and particularly preferably 0.5 to 10 wt % with respect to the weight of the paste. If the adhesive base content exceeds 20 wt %, the paste may be hard, resulting in a decrease in the adhesion. On the other hand, the adhesive base content is less than 0.1 wt %, problems such as lowering of the shape retaining property and deterioration of adhesion to skin may be caused.

From the point of view of the adherence of the present invention, the ratio by weight of the adhesive base and dextrin fatty acid ester is in the range of preferably 1:0.005 to 200 and particularly preferably 1:0.05 to 20.

Examples of the crosslinker of the present invention include synthetic hydrotalcite, dihydroxyaluminum aminoacetate, dried aluminum hydroxide gel, magnesium aluminum silicate, magnesium aluminum metasilicate, aluminum magnesium hydroxide and synthetic aluminum silicate. Of those, dihydroxyaluminum aminoacetate and/or dried aluminum hydroxide gel are/is preferred. Examples of the commercial product of the crosslinker include: Alkamac (manufactured by Kyowa Chemical Industry Co., Ltd.) as a synthetic hydrotalcite; Glycinal SG and Glycinal PG (manufactured by Kyowa Chemical Industry Co., Ltd.) as dihydroxyaluminum aminoacetate; dried aluminum hydroxide gel S-100 (manufactured by Kyowa Chemical Industry Co., Ltd.) as the dried aluminum hydroxide gel; Neusilin UFL2 (FUJI CHEMICAL INDUSTRY CO., LTD.) as magnesium aluminum silicate; Neusilin A and Neusilin (FUJI CHEMICAL INDUSTRY CO., LTD.) and NeoALUMIN S (manufactured by Tomita Pharmaceutical, Co., Ltd.) as magnesium aluminum metasilicate; Sanalmin (manufactured by Kyowa Chemical Industry Co., Ltd.) as aluminum magnesium hydroxide; and synthetic aluminum silicate (manufactured by Kyowa Chemical Industry Co., Ltd. or Tomita Pharmaceutical, Co., Ltd.) as a synthetic aluminum silicate. Those crosslinkers may be used singly or in combination of two or more kinds of them.

The crosslinker content may be in a range generally sufficient for forming a paste in a patch and is preferably 0.001 to 3.0 wt % and particularly preferably 0.001 to 1.5 wt % with respect to the weight of the paste. If the crosslinker content exceeds 3.0 wt %, the paste may be excessively hard, and if the crosslinker content is less than 0.001 wt %, the paste may be soft and some paste may remain on skin in the case of peeling off the patch from skin.

The water content in the present invention may be in a range generally required for a hydrous patch and is preferably 15 to 60 wt % and particularly preferably 20 to 50 wt % with respect to the weight of the paste. If the water content exceeds 60 wt %, the patch is not preferable because the shape retaining property and adherence property of the paste may be significantly lowered. Meanwhile, if the water content is less than 15 wt %, the patch is not preferable because a crosslinking reaction is difficult to occur and some paste may remain on skin in the case of peeling off the patch from skin.

The tackifier resin used in the present invention is a non-water-soluble resin, and examples thereof include ester gum, alicyclic saturated hydrocarbon resins, aliphatic hydrocarbon resins, glycerin ester of hydrogenated rosin, rosin, and terpene resins. Of those, ester gum is preferable. The tackifier resin content may be in a range where the resin is generally contained in the patch and is preferably 2 to 20 wt % and particularly preferably 5 to 20 wt % with respect to the weight of the paste. If the tackifier resin content is less than 2 wt %, there is no effect of improving the adherence of the present invention and improving peeling property when the paste adheres to itself, while the tackifier resin content exceeds 20 wt %, the patch may be difficult to produce or may be highly irritant for skin due to a decrease in the water content.

From the point of view of the adherence of the present invention, the ratio by weight of the tackifier resin and dextrin fatty acid ester is in the range of preferably 1:0.005 to 10 and particularly preferably 1:0.025 to 2.

Examples of the dissolving agent for a tackifier resin used in the present invention include: animal oils such as beef tallow and lard; vegetable oils such as olive oil, sesame oil, and soybean oil; mineral oils such as petrolatum and liquid paraffin; and medium-chain triglycerides, and of those, the mineral oils and/or medium-chain triglycerides are preferable. The dissolving agent content is preferably a minimum amount in consideration of ease in handling in production and is preferably 0.4 to 10 wt % with respect to the weight of the paste. It is not preferable that the dissolving agent content exceeds 10 wt % because the shape-retaining property of the paste is deteriorated.

Examples of the oil absorbing inorganic powder used in the present invention include kaolin, talc, bentonite, montmorillonite, zinc oxide, titanium oxide, and silicic anhydride, and of those, kaolin is preferable. Those components have oil absorbing ability of 20 to 400 v/w % and may be used singly or in combination of two or more of them. The oil absorbing inorganic powder content may be in a range where the powder is generally contained in the patch and is preferably 0.1 to 30 wt %, particularly preferably 1 to 15 wt % with respect to the weight of the paste. If the oil absorbing inorganic powder content is less than 0.1 wt %, it is not substantially effective to blend the powder. It is not preferable that the oil absorbing inorganic powder content exceeds 30 wt % because the paste becomes hard and loses flexibility.

In the hydrous external skin patch of the present invention, the thickness of the paste is 100 to 1,000 μm. In general, if the thickness of the paste increases, the adherence increases while the flexibility decreases. As a result, the patch has increased uncomfortable feeling in application and is easy to drop. A conventionally known hydrous molded cataplasm has relatively low adherence and is required to have a certain level of thickness to achieve a certain level of adherence, so it is difficult to avoid the problem of dropping in application. The hydrous external skin patch of the present invention has sufficient adherence even if the thickness of the paste decreases, and in order to improve the utility, it is preferable to decrease the thickness of the paste as much as possible. However, if the thickness of the paste decreases, drug quantities which may be blended becomes small. Therefore, in the hydrous external skin patch of the present invention, the thickness of the paste is 100 to 1,000 μm, preferably 100 to 800 μm.

In the paste of the external skin patch of the present invention, additives which may be used in a usual paste may be appropriately blended depending on the purpose in addition to the above-mentioned components. Examples of the additives include hardening adjusters, solvents, absorption enhancers, stabilizers, and surfactants. Those additives may be used singly or in combination of two or more of them.

Examples of the hardening adjuster include citric acid, malic acid, tartaric acid, disodium edetate, sodium metaphosphate, gluconic acid, and lactic acid. The content of the hardening adjuster is preferably 0.001 to 3 wt % and particularly preferably 0.01 to 2 wt % with respect to the weight of the paste.

Examples of the solvent include: polyvalent alcohols such as (concentrated) glycerin, D-sorbitol liquid, propylene glycol, dipropylene glycol, ethylene glycol, macrogol, diethyleneglycol, 1,3-butyleneglycol, 2-ethyl-1,3-hexanediol, and polypropylene glycol 2000; monovalent alcohols such as ethanol, isopropanol, benzyl alcohol, stearyl alcohol, and oleyl alcohol; esters of a medium-chain triglyceride having 6 to 12 carbon atoms such as triacetin, diisopropyl sebacate, diethyl sebacate, and triisooctanoic acid; and ketones such as crotamiton. Those solvents may be used singly or in combination of two or more kinds of them. The content of the solvent is preferably 1 to 60 wt % and particularly preferably 2 to 50 wt % with respect to the weight of the paste.

Examples of the absorption enhancer include L-menthol, oleic acid, diisopropyl adipate, and isopropyl myristate. When L-menthol is used as the absorption enhancer, the content of the L-menthol is 0.01 to 10 wt % and particularly preferably 0.1 to 5.0 wt % with respect to the weight of the paste.

Examples of the stabilizer include: phenolic substances such as methyl parahydroxybenzoate and propyl parahyroxybenzoate; neutral substances such as chlorobutanol and phenylethyl alcohol; inverted soaps such as benzalkonium chloride and benzethonium chloride; antioxidants such as vitamin E, butylhydroxyanisol, tocopherol acetate, propyl gallate, and 2-mercaptobenzimidazole; reductants such as ascorbic acid, sodium hydrogen sulfite, and sodium thiosulfate; and chelating agents such as sodium edetate. The content of the stabilizer is preferably 0 to 1 wt % and particularly preferably 0.001 to 0.5 wt % with respect to the weight of the paste.

Examples of the surfactant include: anionic surfactants such as sodium lauryl sulfate; cationic surfactants such as cetylpyridinium chloride; and nonionic surfactants such as glyceryl monostearate, sucrose fatty acid ester, polyoxyethylene hydrogenated caster oil, polyoxyethylene sorbitan fatty acid ester, polyoxyethylene fatty acid ester, and polyoxyethylene alkyl ether. The content of the surfactant is preferably 0 to 3 wt % and particularly preferably 0.01 to 1 wt % with respect to the weight of the paste.

For example, in the case where the adhesion of the paste of the present invention is measured in accordance with the adhesion test described in Drug Approval and Licensing Procedures in Japan (Test Example 1 below), the test result is preferably more than No. 4 of the steel ball shown in Table 1, particularly preferably more than No. 5. If the level is less than No. 4, the patch is not preferable because the patch is easily peeled off in application.

The hydrous external skin patch of the present invention has a laminate structure of a support, a paste, and a liner. Examples of the support include non-woven fabric or woven fabric formed of cotton, polyester, rayon, nylon, polyolefin, polyethylene, vinylon, acetate, polypropylene, and polyurethane or the like. Examples of the liner include a plastic-based liner formed of polyester, polyethylene and polypropylene, a cellulose-based liner, the liner coated with a silicon-based release agent, and a paper sheet or the like. The plastic-based liner formed of polyester, polyethylene and polypropylene is particularly preferred.

The method of producing the patch of the present invention may employ a usual formulation method. For example, a patch may be manufactured by spreading a paste between a non-woven or woven fabric surface of a support and a liner.

EXAMPLES

Hereinafter, the present invention will be described specifically with reference to Examples and Test examples. However, the present invention is not limited thereto.

Example 1

Indometacin (1 part by weight), crotamiton (2 parts by weight), partially neutralized polyacrylic acid (3.5 parts by weight), carmellose sodium (3 parts by weight), concentrated glycerin (22 parts by weight), kaolin (3 parts by weight), gelatin (1 part by weight), dihydroxyaluminum aminoacetate (0.30 parts by weight) and lactic acid (1.25 parts by weight) were blended with purified water (35 parts by weight), and ester gum (10 parts by weight) dissolved in light liquid paraffin (2.50 parts by weight) with heating and dextrin palmitate (2 parts by weight) were added thereto. Then, purified water was added so that the total amount was 100 parts by weight, and the whole was stirred with a stirrer until the mixture became homogeneous, to thereby prepare a composition. The composition was spread and applied on a liner film made of polyester and coated with a polyester stretch woven fabric, followed by cutting into pieces each having a size of 10 cm×7 cm, to thereby obtained a patch 1.

Example 2

The same procedures as in Example 1 were repeated except that the amount of dextrin palmitate blended in Example 1 was changed from 2 parts by weight to 5 parts by weight, to thereby obtained a patch 2.

Example 3

The same procedures as in Example 1 were repeated except that 2 parts by weight of dextrin palmitate in Example 1 was replaced by 2 parts by weight of dextrin myristate, to thereby obtained a patch 3.

Example 4

The same procedures as in Example 1 were repeated except that the amount of dextrin palmitate blended in Example 1 was changed from 2 parts by weight to 0.5 parts by weight, to thereby obtained a patch 4.

Example 5

The same procedures as in Example 1 were repeated except that the amount of dextrin palmitate blended in Example 1 was changed from 2 parts by weight to 1 part by weight, to thereby obtained a patch 5.

Comparative Example 1

The same procedures as in Example 1 were repeated except that dextrin palmitate in Example 1 was not blended, to thereby obtained a patch 6.

Test Example 1

Adhesion Test (i) Ball Tack Test

The patches 1 to 6 obtained two weeks ago were used to perform the following test.

A tilt table (height 18 cm, tilt angle 30°) was prepared, and each patch was cut into a piece of 5 cm×3 cm. Then, the piece was fixed by using a double-stick tape on the table at 10 cm from the top of the slope with the adhesive layer surface-side up at a longitudinal-side length of 5 cm, and the rest of the slope was covered with paper so that the difference in height between the patch portion and the rest of the slope was eliminated (FIG. 1). Thereafter, a series of steel balls shown in Table 1 were rolled from the upper end of the slope in ascending order of size, and the maximum size of steel balls which stopped for 10 seconds on the adhesive surface of the patch was determined. The procedures were repeated three times, and the average value of the maximum sizes of the steel balls was calculated to determine an adhesion of each patch. The results are shown in Table 2.

TABLE 1

| | Type of steel balls | |
|---|---|---|
| No. (Size) | Diameter (mm) | Weight (g) |
| 1 | 3.2 | 0.1 |
| 2 | 4.8 | 0.4 |
| 3 | 6.4 | 1.0 |
| 4 | 7.9 | 2.0 |
| 5 | 9.5 | 3.5 |
| 6 | 11.1 | 5.6 |
| 7 | 12.7 | 8.3 |
| 8 | 14.3 | 11.9 |
| 9 | 15.9 | 16.3 |
| 10 | 17.5 | 21.7 |
| 11 | 19.1 | 28.1 |
| 12 | 20.6 | 35.8 |
| 13 | 22.2 | 44.7 |
| 14 | 23.8 | 54.9 |
| 15 | 25.4 | 66.7 |
| 16 | 27.0 | 80.0 |
| 17 | 28.9 | 94.9 |
| 18 | 30.2 | 111.6 |
| 19 | 31.8 | 130.2 |
| 20 | 33.3 | 150.7 |

(ii) Probe Tack Test

Figure 2:
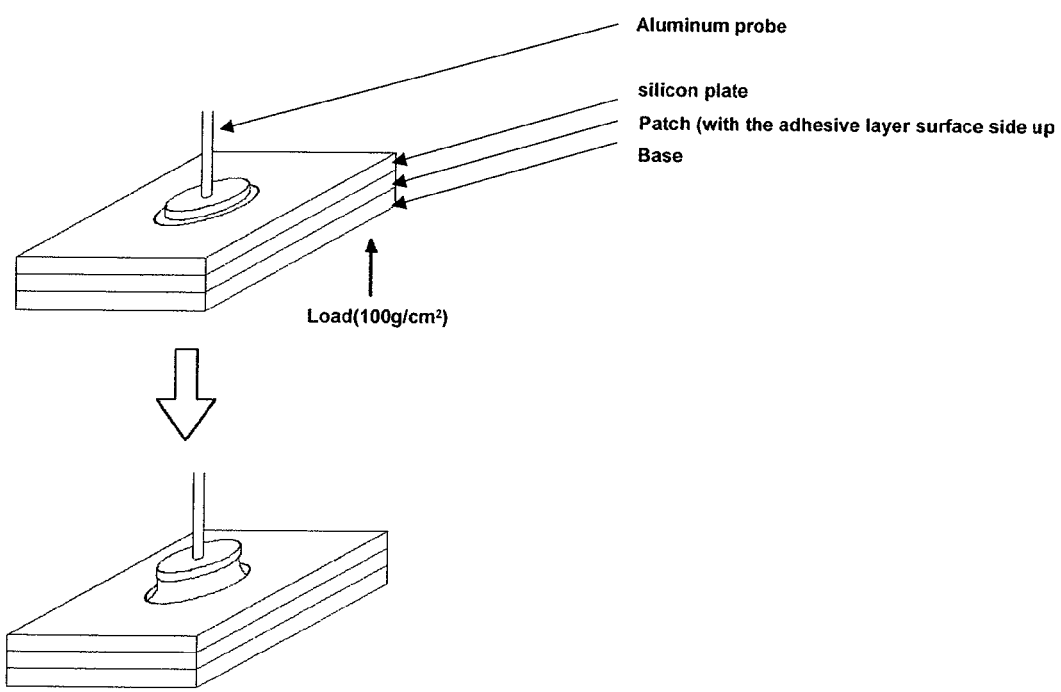
FIG. 2 is a schematic view illustrating a device used in an adhesion test (ii).

The patches 1 and 4 to 6 were cut into pieces each having a size of 5×7 cm, and each piece was fixed on a base with a double-stick tape with the adhesive layer surface side up. Then, a silicon plate having a hole with a diameter of 22 mm and having a thickness of 1 mm was placed on the adhesive layer surface. A load of 100 g/cm$^2$ was applied to the adhesive layer surface (in part of the hole in the silicon plate) using an aluminum probe with a diameter of 20 mm for 1 second (FIG. 2), and the maximum load (g) during peeling off the piece from the probe at a rate of 10 mm/sec was measured using a texture analyzer TA-TAi (manufactured by Eko Instruments Co., Ltd.). The results are shown in Table 2.

Test Example 2

Water Absorption Test

The weights of the patches 1 to 6 (10 cm×7 cm) and a nonwoven fabric having the same area were measured, and the patches and fabric were immersed in 100 mL of an aqueous solution of 0.5% sodium chloride at 35° C. for 2 hours. Then, water on the surfaces was wiped off, and the weights were measured again, followed by calculation of the amount (g) of water absorbed in each patch using the following formula. The results are shown in Table 2.

Amount of water absorbed(g)=$(W3-W4)-(W1-W2)$

W1: Weight of each patch before immersion (g)

W2: Weight of nonwoven fabric before immersion (g)

W3: Weight of each patch after immersion (g)

W4: Weight of nonwoven fabric after immersion (g)

Test Example 3

Sensory Evaluation

The patches 1 to 3 and 6 (10 cm×7 cm) were simultaneously applied to the lower back and elbow of each of 20 men under sweating conditions (for example, upon taking a sauna and playing golf) for 3 hours or more, and the patches just before peeling were evaluated in accordance with the VAS (Visual Analogue Scale) method [on a scale including the left end defined as 0 cm (the patch is not applied on skin) and the right end defined as 10 cm (the patch is completely applied on skin), sensory positions of each subject are recorded to determine the length from the left end]. The average values thereof are shown in Table 2.

Test Example 4

Paste-to-Paste Adhesion Test

For each of the patches 1 to 6 (10 cm×7 cm), the long-side was folded in half to bond the paste to itself, and a load of 2 kg was applied to the patch for one minute. One minute later, the paste was peeled off by hand, and each patch was evaluated based on the following criteria. The results are shown in Table 2.

<Criteria for Judgment>
○: Good peeling property (the patch is easy to peel off without deformation of the support)
x: Bad peeling property (the patch is difficult to peel off enough to deform the support)

TABLE 2

| Component | Patch 1 | Patch 2 | Patch 3 | Patch 4 | Patch 5 | Patch 6 |
|---|---|---|---|---|---|---|
| Indometacin | 1.00 | 1.00 | 1.00 | 1.00 | 1.00 | 1.00 |
| Crotamiton | 2.00 | 2.00 | 2.00 | 2.00 | 2.00 | 2.00 |
| Partially neutralized polyacrylic acid | 3.50 | 3.50 | 3.50 | 3.50 | 3.50 | 3.50 |
| Carmellose sodium | 3.00 | 3.00 | 3.00 | 3.00 | 3.00 | 3.00 |
| Ester gum | 10.00 | 10.00 | 10.00 | 10.00 | 10.00 | 10.00 |
| Concentrated glycerin | 22.00 | 22.00 | 22.00 | 22.00 | 22.00 | 22.00 |
| Kaolin | 3.00 | 3.00 | 3.00 | 3.00 | 3.00 | 3.00 |
| Gelatin | 1.00 | 1.00 | 1.00 | 1.00 | 1.00 | 1.00 |
| Dextrin palmitate | 2.00 | 5.00 | — | 0.50 | 1.00 | — |
| Dextrin myristate | — | — | 2.00 | — | — | — |
| Light liquid paraffin | 2.50 | 2.50 | 2.50 | 2.50 | 2.50 | 2.50 |
| Dihydroxyaluminum aminoacetate | 0.30 | 0.30 | 0.30 | 0.30 | 0.30 | 0.30 |
| Lactic acid | 1.25 | 1.25 | 1.25 | 1.25 | 1.25 | 1.25 |
| Purified water | 48.45 | 45.45 | 48.45 | 49.95 | 49.45 | 50.45 |
| Total | 100.00 | 100.00 | 100.00 | 100.00 | 100.00 | 100.00 |
| Test Example 1-(i) | 17.0 | 18.0 | 16.0 | 16.0 | 16.5 | 14.3 |
| Test Example 1-(ii) | 293.3 | — | — | 269.6 | 303.8 | 182.8 |
| Test Example 2 | 5.3 | 6.3 | 4.2 | 4.4 | 4.8 | 3.5 |
| Test Example 3 Lower back | 8.5 | 8.4 | 8.7 | — | — | 6.2 |
| Elbow | 8.6 | 8.2 | 8.8 | — | — | 5.8 |
| Test Example 4 | ○ | ○ | ○ | ○ | ○ | x |

Table 2 reveals that the patches of the present invention have improved adhesion compared with the patch of Comparative Example (Test Examples 1-(i) and (ii)). In addition, the patches of the present invention can be easily peeled off if the pastes adhere to themselves and can be used again (Test Example 4). Moreover, the patches of the present invention have improved water-absorbing ability (Test Example 2), and it is obvious that the patches are excellent in adherence even under sweating conditions (Test Example 3).

Meanwhile, for the patches of the present invention, indometacin-absorbing test and drug efficacy test were performed using rats. As a result, in all the patches, indometacin serving as an active ingredient was immediately absorbed in skin and muscle to provide high analgesic activity and anti-inflammatory activity. Therefore, dextrin fatty acid ester was found to have no effect on expression of the drug efficacy of the active ingredient.

What is claimed is:

1. A hydrous external skin patch, comprising an adhesive layer comprising 0.1 to 10 wt. % of a drug, 0.1 to 20 wt. % of an adhesive base, 0.001 to 3.0 wt. % of a crosslinker, 15 to 60 wt. % of water, 2 to 20 wt. % of a tackifier resin, 0.4 to 10 wt. % of a dissolving agent for the tackifier resin, 0.1 to 30 wt. % of an oil absorbing inorganic powder, and 0.1 to 20 wt. % of a dextrin fatty acid ester, wherein the skin patch has a thickness of 100 to 1,000 μm and wherein the dextrin fatty acid ester comprises dextrin palmitate, dextrin myristate, dextrin laurate and/or dextrin stearate.

2. The hydrous external skin patch according to claim 1, wherein the drug comprises a nonsteroidal anti-inflammatory drug.

3. The hydrous external skin patch according to claim 1, wherein the adhesive base is one kind or two more kinds selected from polyacrylic acid, partially neutralized polyacrylic acid, and completely neutralized polyacrylic acid.

4. The hydrous external skin patch according to claim 1, wherein the crosslinker comprises dihydroxyaluminum aminoacetate and/or dried aluminum hydroxide gel.

5. The hydrous external skin patch according to claim 1, wherein the tackifier resin comprises ester gum.

6. The hydrous external skin patch according to claim 1, wherein the dissolving agent comprises mineral oil and/or medium-chain triglyceride.

7. The hydrous external skin patch according to claim 1, wherein the oil absorbing inorganic powder comprises kaolin.

* * * * *